US012766092B2

(12) United States Patent
Kugelman

(10) Patent No.: US 12,766,092 B2
(45) Date of Patent: Oct. 20, 2026

(54) COSMETIC COMPOSITIONS COMPRISING A CACTUS FLOWER EXTRACT COMPLEX

(71) Applicant: SKG Beauty Holdings, Inc, New York, NY (US)

(72) Inventor: Sarah Kugelman, New York, NY (US)

(73) Assignee: SKG Beauty Holdings, Inc, New York, NY (US)

( * ) Notice: Subject to any disclaimer, the term of this patent is extended or adjusted under 35 U.S.C. 154(b) by 293 days.

(21) Appl. No.: 18/611,998

(22) Filed: Mar. 21, 2024

(65) Prior Publication Data

US 2025/0295576 A1 Sep. 25, 2025

(51) Int. Cl.

| | |
|---|---|
| ***A61K 8/9789*** | (2017.01) |
| ***A61K 8/34*** | (2006.01) |
| ***A61K 8/9733*** | (2017.01) |
| ***A61Q 19/00*** | (2006.01) |

(52) U.S. Cl.

CPC ............ *A61K 8/9789* (2017.08); *A61K 8/345* (2013.01); *A61K 8/9733* (2017.08); *A61Q 19/00* (2013.01); *A61K 2800/10* (2013.01); *A61K 2800/85* (2013.01)

(58) Field of Classification Search

CPC .................................................... A61K 8/9789

See application file for complete search history.

(56) References Cited

FOREIGN PATENT DOCUMENTS

| | | | | |
|---|---|---|---|---|
| BR | 102013028228 A2 * | 9/2015 | ............... | A61K 8/88 |
| CN | 112386541 A * | 2/2021 | ............. | A61K 8/347 |

* cited by examiner

*Primary Examiner* — Qiuwen Mi

(74) *Attorney, Agent, or Firm* — Grant Attorneys at Law PLLC; Kristin Grant

(57) ABSTRACT

A composition comprising a cactus flower extract complex.

8 Claims, 3 Drawing Sheets

COSMETIC COMPOSITIONS COMPRISING A CACTUS FLOWER EXTRACT COMPLEX

BACKGROUND

Field of Invention

The present disclosure relates generally to topical cosmetic compositions, and particularly to topical cosmetic compositions comprising a cactus flower extract complex.

Related Art

Deionized water, also known as demineralized water or distilled water, is water that has had its ions removed, typically through processes like distillation or ion exchange. In skincare and haircare formulations, deionized water is often used as a base or solvent. There are some advantages to using deionized water in cosmetic formulations. For example, deionized water is highly purified, lacking impurities and minerals. This purity contributes to a consistent and reproducible product formulation. Skincare and haircare products formulated with deionized water are less likely to vary in terms of texture, color, or scent due to regional differences in water quality. Deionized water provides a neutral and customizable base for cosmetic formulations. Formulators can precisely control the composition of the product, allowing for the incorporation of specific actives, botanical extracts, or other beneficial ingredients without interference from minerals present in regular water.

Deionized water present in a skincare or haircare products, on its own, does not provide hydration or other benefits to the skin or hair. The human skin is made up mostly of water enriched with minerals and electrolytes necessary for cellular processes. Deionized water typically exists in cosmetic formulations at high percentages as hypotonic solutions. Hypotonic solutions contain more water than minerals and electrolytes and can cause human cells to swell. An isotonic solution has an equal balance of minerals, electrolytes and water, creating a balanced osmotic pressure in the cells.

The present disclosure uses a complex containing a cactus flower extract complex as a replacement for deionized water in topical cosmetic formulations. The cactus flower extract complex being a mineral and electrolyte enriched isotonic solution, reducing the risk of osmotic pressure or stress on the skin that comes with the use of deionized water.

In embodiments of the present inventions, the cactus flower extract complex is used as the sole solvent, enhancing the benefits provided by the formulations' active ingredients, providing minerals without being irritating, and eliminating the need for deionized or other water types as solvents in the product. Unlike deionized water, the cactus flower extract complex provides electrolyte balance. The present inventions provide nutrient rich isotonic solutions that are much more favorable cellular environments than deionized water or other hypo/hyper-tonic solutions.

SUMMARY OF INVENTION

It is to be understood that the phraseology and terminology employed herein are for the purpose of the description and should not be regarded as limiting.

The present disclosure is directed to topical cosmetic compositions comprising a cactus flower extract complex. The cactus flower extract complex includes at least *Opuntia ficus-indica* fruit extract, 2,3-butanediol, and *Usnea barbata* (Lichen) Extract. The topical cosmetic compositions may also comprise an adaptogen complex including at least wheatgrass (*Pascopyron smithii*), amla (*Phyllanthus emblica*), ginseng (*Panax ginseng*), and ashwagandha (*Withania somnifera*).

These and other features will become readily apparent upon further review of the specification, drawings, and claims.

BRIEF DESCRIPTION OF THE DRAWINGS

Embodiments of the present invention will be described by way of example only, and not limitation, with reference to the accompanying drawings.

DETAILED DESCRIPTION

The present disclosure relates to topical cosmetic compositions comprising a cactus flower extract complex obtained through the processing of a byproduct of a fermentation process used to produce water kefir PHA (with INCI name Water & *Optunia Ficus-Indicia* Fruit Extract & *Lactobacillus* Ferment).

Figure 1:
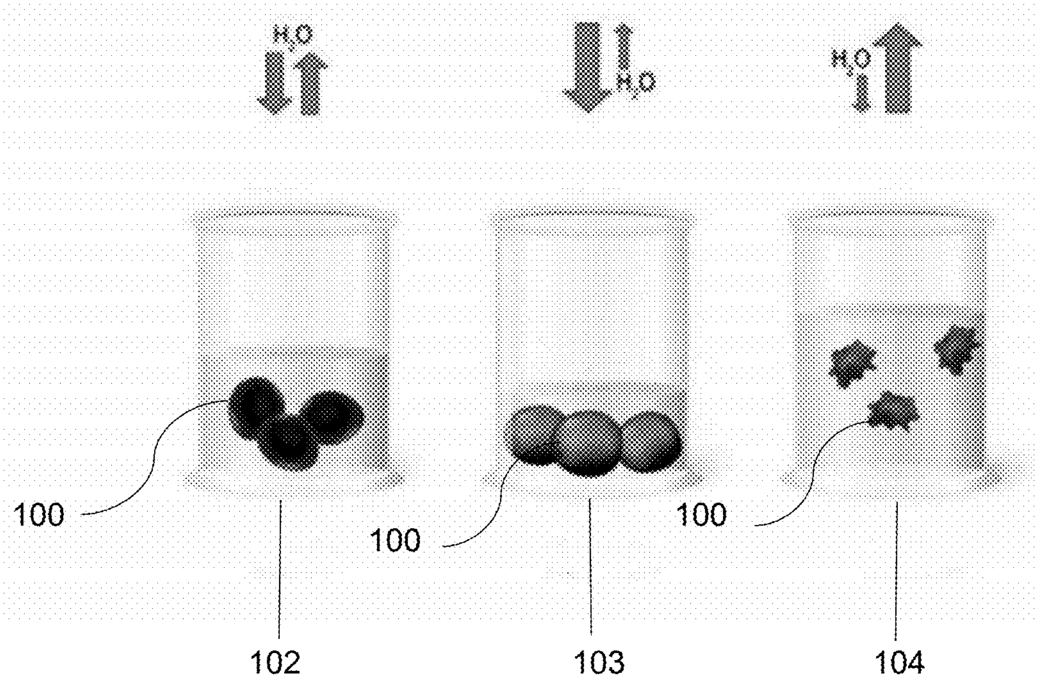
FIG. 1 is a diagram showing the effect on cells when placed in various solutions.

Deionized water is typically used as the solvent in many skincare and haircare compositions. Cosmetic compositions that are free of water typically use an oil in place of water. Deionized water exists in cosmetic formulations at high percentages as hypotonic solutions. Hypotonic solutions contain more water than minerals and electrolytes and can cause human cells to swell. An isotonic solution has an equal balance of minerals, electrolytes and water, creating a balanced osmotic pressure in the cells. FIG. 1 is a diagram showing the effect on cells 100 when placed in isotonic 102, hypotonic 103, and hypertonic solutions 104.

An osmotic pressure cell membrane comparisons assay was conducted to assess the effect of the cactus flower extract complex of the disclosed inventions on keratinocyte membrane integrity and cell volume. The keratinocytes were exposed to the test substance and control, after which images were analyzed for membrane integrity and cell size.

Keratinocytes were seeded into a 24-well plate and grew to confluency in complete media. Complete media was removed from all wells followed by a washing procedure with phosphate buffered saline. 1 mL of the 100% cactus flower extract or deionized water were added to designated wells. Initial images (T=0) of the cells were taken using a 40× objective. 45 minutes later, a subsequent image (T=45) of the same cluster of cells was taken. Next, the test substance or control was removed and wells were washed with phosphate buffered saline. 1 mL of paraformaldehyde fixative was added to all wells and incubated for 10 minutes at 25° C., after which the paraformaldehyde fixative was removed and all wells were washed with phosphate buffered saline. 1 mL of the crystal violet stain was added to all wells for 30 minutes at 25° C., after which wells were washed continuously with phosphate buffered saline until clear. The crystal violet stain was used for enhanced microscopy imaging and a final stain image was taken of the test well.

A select number of cells were traced using ImageJ software to determine changes in cell size after 45 minutes of treatment.

Percent change is expressed relative to complete media and calculated by the following equation:

$$\text{Percent Change (\%)} = \frac{\text{Cell Size}_{T=45} - \text{Cell Size}_{T=0}}{\text{Cell Size}_{T=0}} \times 100$$

Figure 2:
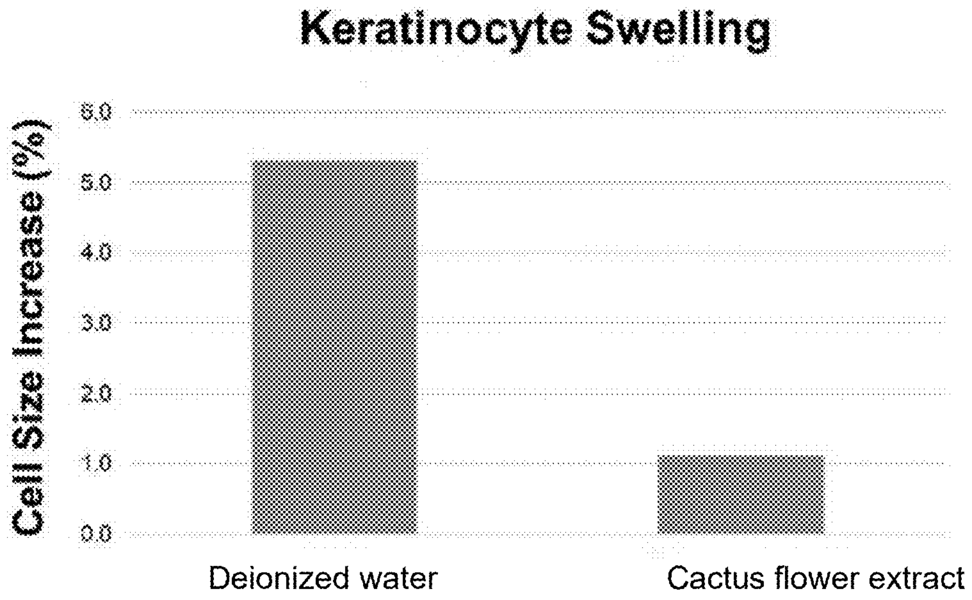
FIG. 2 is a bar chat showing the effect of deionized water and the bio-fermented cactus flower extract complex on cell volume.
Figure 3:
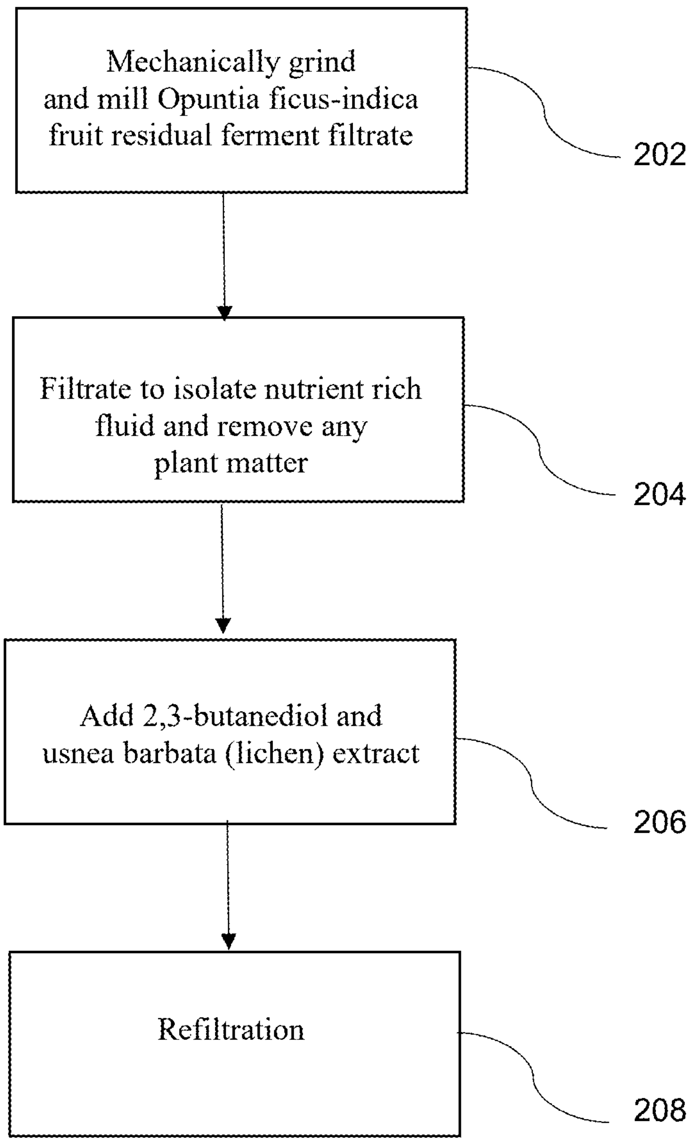
FIG. 3 is a flow chart showing a method of manufacturing the cactus flower extract complex.

The results of this study revealed that keratinocytes exposed to deionized water demonstrated an increase in cell volume, whereas keratinocytes incubated with the cactus flower extract complex did not exhibit a large increase in cell volume. FIG. 2 is a bar chart showing the effect of deionized water and the cactus flower extract complex on cell volume after treatment.

The cactus flower extract complex preferably includes at least *Opuntia ficus-indica* Fruit Extract, 2,3-Butanediol, and *Usnea barbata* (Lichen) Extract. The amount of the cactus flower extract complex used in cosmetic formulations would be equivalent to the amount of deionized water that would have been used in that same product. To manufacture the disclosed cactus flower extract, the *Opuntia ficus-indica* fruit residual ferment filtrate from water kefir PHA is mechanically ground and milled 202 and then filtrated to isolate nutrient rich fluid and remove any plant matter 204. 2,3-butanediol and *Usnea barbata* (lichen) extract is added 206. Batch refiltration is performed, if needed 208.

In embodiments where an adaptogen complex is present it preferably includes wheatgrass (*Pascopyron smithii*), amla (*Phyllanthus emblica*), ginseng (*Panax ginseng*), and ashwagandha (*Withania somnifera*). Adaptogens are known to help alleviate stress on the skin and promote hair growth. The specific combination of adaptogenic herbs in the adaptogen complex are thought to amplify each other's efficacy when combined.

This disclosure is not intended to limit the invention to the particular composition disclosed, but, to the contrary, the intention is to cover all modifications, equivalents, and alternatives falling within the scope of the claims.

The invention claimed is:

1. A cosmetic composition for topical application to the skin or hair, comprising a cactus flower extract complex, wherein the cactus flower extract complex is derived from the processing of residual ferment filtrate of water kefir polyhydroxy acid, and wherein the cactus flower extract complex comprises 2,3-butanediol.

2. The cosmetic composition of claim 1, wherein the cactus flower extract complex comprises *Opuntia ficus-indica* fruit extract.

3. The cosmetic composition of claim 1, wherein the cactus flower extract complex comprises *Usnea barbata* extract.

4. The cosmetic composition of claim 1, further comprising an adaptogen complex.

5. The cosmetic composition of claim 4, wherein the adaptogen complex comprises Wheatgrass.

6. The cosmetic composition of claim 4, wherein the adaptogen complex comprises Amla.

7. The cosmetic composition of claim 4, wherein the adaptogen complex comprises Ginseng.

8. The cosmetic composition of claim 4, wherein the adaptogen complex comprises Ashwagandha.

* * * * *